United States Patent [19]

Rentzea et al.

[11] 4,198,423

[45] Apr. 15, 1980

[54] 1,3-BIS-(TRIHALOMETHYLSULFENYL)-IMIDAZOLINE-2,4-DIONES

[75] Inventors: Costin Rentzea, Heidelberg; Ernst-Heinrich Pommer, Limburgerhof; Celia J. Mappes, Boehl-Iggelheim; Bernd Zeeh, Ludwigshafen, all of Fed. Rep. of Germany

[73] Assignee: BASF Aktiengesellschaft, Fed. Rep. of Germany

[21] Appl. No.: 22,161

[22] Filed: Mar. 20, 1979

[51] Int. Cl.² ............... A01N 9/12; C07D 233/80
[52] U.S. Cl. ............................ 424/273 R; 548/311
[58] Field of Search ............... 548/311; 424/273 R

[56] References Cited

U.S. PATENT DOCUMENTS 2,886,487  5/1959  Kupferberg et al. ............... 548/311

FOREIGN PATENT DOCUMENTS 1168914  4/1964  Fed. Rep. of Germany ........... 548/311
967166   8/1964  United Kingdom .................. 548/311
967167   8/1964  United Kingdom .................. 548/311
972008  10/1964  United Kingdom .................. 548/311

OTHER PUBLICATIONS

Lien et al., Pestic. Biochem. Physiol. 1974, vol. 4, pp. 289–298.

*Primary Examiner*—Natalie Trousof
*Attorney, Agent, or Firm*—Keil & Witherspoon

[57] ABSTRACT

New 1,3-bis-(trihalomethylsulfenyl)-imidazoline-2,4-diones and their use as fungicides.

4 Claims, No Drawings

1,3-BIS-(TRIHALOMETHYLSULFENYL)-IMIDAZOLINE-2,4-DIONES

The present invention relates to new and valuable 1,3-bis-(trihalomethylsulfenyl)-imidazoline-2,4-diones and their use as fungicides.

It is known (E. J. Lien and co-workers, Pestic. Biochem. and Physiol., 4, 289, 1974) that bis S-CCl$_3$ derivatives of 5,5-diphenyl- and 5-ethyl-5-phenylimidazoline-2,4-dione have fungicidal properties.

We have now found that new imidazoline-2,4-dione derivatives of the formula

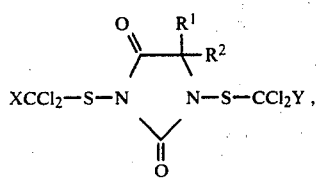

where X and Y are identical or different and each denotes chlorine or fluorine, and R$^1$ and R$^2$ are identical or different and each denotes hydrogen or lower alkyl (C$_1$-C$_4$), or R$^1$ and R$^2$ are directly linked with each other, or together denote the radical —(CH$_2$)$_n$—, n denoting one of the integers 1, 2, 3, 4, 5 and 6, have a strong fungicidal action. The new compounds have a broad spectrum of action and may be used especially on Phycomycetes and *Fungi imperfecti*, but also on Ascomycetes and Basidiomycetes. The new compounds are for example particularly suitable for protecting plants against phytopathogenic fungi, e.g., *Plasmopara viticola* in grapes, *Pseudoperonospora humuli* in hops, *Phytophthora infestans* in potatoes and tomatoes, *Pythium ultimum* in pea seedlings, *Botrytis cinerea* in grapes, strawberries and pimientos, *Septoria nodorum* in cereals, and *Venturia inaequalis* (scab) in apple trees. In the concentrations necessary for combating fungi, the compounds cause no damage to crop plants.

We have further found that compounds of the formula I are obtained by reacting an imidazoline-2,4-dione of the formula

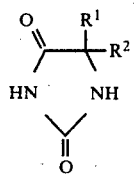

with a sulfenyl chloride of the formula XCCl$_2$—S—Cl (IIIa) or YCCl$_2$—S—Cl (IIIb), R$^1$, R$^2$, X and Y having the above meanings, if desired in the presence of an acid binder and if desired in the presence of a diluent.

The compounds of the formula I may also be obtained by reacting an imidazoline-2,4-dione of the formula

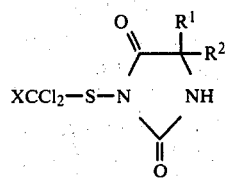

R$^1$, R$^2$ and X having the above meanings, with a sulfenyl chloride of the formula IIIb, if desired in the presence of an acid binder and if desired in the presence of a diluent.

The compounds of the formula I according to the invention may further be obtained by reacting an N-cyclopropylimidazoline-2,4-dione of the formula

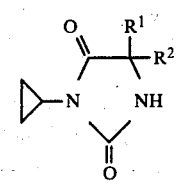

with a sulfenyl chloride of the formula XCCl$_3$—S—Cl (IIIa) or YCCl$_2$—S—Cl (IIIb), R$^1$, R$^2$, X and Y having the above meanings, with elimination of the cyclopropyl group as allyl chloride and if desired in the presence of an acid binder and if desired in the presence of a diluent.

Finally, the compounds of the formula I according to the invention in which X or X and Y denote fluorine may be obtained by reacting an imidazoline-2,4-dione of the formula

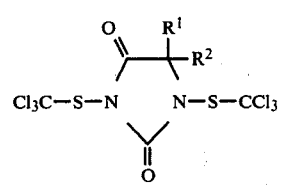

R$^1$ and R$^2$ having the above meanings, with anhydrous hydrofluoric acid, in order to exchange one or two fluorine atoms in the trichloromethylthio side chain for one or two chlorine atoms.

The first three of the above reactions according to the invention of imidazoline-2,4-diones of the formulae II, IV and V are advantageously carried out in solvents or diluents inert to the reactants, e.g., toluene, xylene, diethyl ether, tetrahydrofuran, dioxane, dimethoxyethane, acetone, methyl ethyl ketone, ethyl acetate, methylene chloride, and chloroform.

The reaction with a compound of the formula VI can be carried out in an excess of hydrofluoric acid as diluent.

Examples of suitable acid binders are inorganic bases such as hydroxides or carbonates of alkali metals and alkaline earth metals (e.g., NaOH, Na$_2$CO$_3$), and particularly tertiary amines, such as triethylamine, dimethylaniline, and pyridine.

The reactions are carried out at, for instance, from −30° to +100° C., preferably from −10° to +25° C., and at atmospheric pressure. The imidazoline-2,4-diones of the formulae II and IV used as starting materials are known from the literature and may be prepared in accordance with Bucherer (J. Prakt. Chem., 140, 303, 1934) or Cremlyn (J. Chem. Soc. 6240, 1964).

The first reaction described above, employing a compound of the formula II, is preferred.

The compounds of the formula I according to the invention are colorless crystalline products readily soluble in ethyl acetate, acetone, ethanol, tetrahydrofuran, methylene chloride, chloroform, dimethyl sulfoxide, dimethylformamide, and N-methylpyrrolidone.

Individual examples of the new active ingredients are given below (the imidazoline-2,4-diones are designated "hydantoins" in the following):
1,3-bis-(trichloromethylthio)-hydantoin
1,3-bis-(dichlorofluoromethylthio)-hydantoin
1-trichloromethylthio-3-dichlorofluoromethylthiohydantoin
1-dichlorofluoromethylthio-3-trichloromethylthiohydantoin
1,3-bis-(trichloromethylthio)-5-methylhydantoin
1,3-bis-(dichlorofluoromethylthio)-5-methylhydantoin
1,3-bis-(trichloromethylthio)-5,5-dimethylhydantoin
1,3-bis-(dichlorofluoromethylthio)-5,5-dimethylhydantoin
1,3-bis-(trichloromethylthio)-5-methyl-5-ethylhydantoin
1-dichlorofluoromethyl-3-trichloromethylthio-5-methyl-5-ethylhydantoin
1,3-bis-(trichloromethylthio)-trans-cyclohexanespiro-5-hydantoin
1,3-bis-(dichlorofluoromethylthio)-trans-cyclohexanespiro-5-hydantoin.

The manufacture of the active ingredients is illustrated by the following examples.

EXAMPLE 1

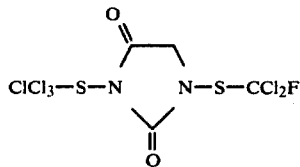

At about 0° to +5° C., 16.9 g (0.1 mole) of dichlorofluoromethylsulfenyl chloride and subsequently 10.1 g (0.1 mole) of triethylamine are dripped, while stirring thoroughly, into a suspension of 24.9 g (0.1 mole) of 3-trichloromethylthiohydantoin in 200 ml of anhydrous ethyl acetate. After stirring for 2 hours at room temperature (20° C.) the precipitated triethylamine hydrochloride is filtered off and washed with 50 ml of ethyl acetate. The filtrate is extracted by shaking with 250 ml of water, dried, clarified with 1 g of animal charcoal, and concentrated. The residue crystallizes at 0° C. after the addition of 50 ml of n-pentane. There is obtained 31.3 g (82% of theory) of 1-dichlorofluoromethylthio-3-trichloromethylthiohydantoin; m.p.: 114°–116° C.

The 3-trichloromethylthiohydantoin (m.p.: 184° C.) used as starting material was prepared in accordance with R. J. W. Cremlyn (J. Chem. Soc., 6240, 1964).

EXAMPLE 2

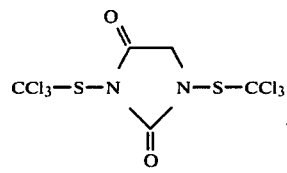

(a) At about 0° C., 37.2 g (0.2 mole) of trichloromethylsulfenyl chloride and subsequently 20.2 g (0.2 mole) of triethylamine are dripped, while stirring thoroughly, into a suspension of 10 g (0.1 mole) of hydantoin in 150 ml of anhydrous ethyl acetate. After stirring for 90 minutes at room temperature, the precipitated triethylamine hydrochloride is filtered off and washed with 100 ml of ethyl acetate. The filtrate is concentrated and the residue is crystallized by trituration with n-pentane. There is obtained 36.1 g (90.5% of theory) of 1,3-bis-(trichloromethylthio)-hydantoin; m.p.: 142° C.

(b) At about 25° C., 37.2 g (0.2 mole) of trichloromethylsulfenyl chloride and subsequently 20.2 g (0.2 mole) of triethylamine are dripped, while stirring thoroughly, into a suspension of 14.0 g (0.1 mole) of 3-cyclopropylhydantoin in 150 ml of anhydrous hydantoin. After stirring for 12 hours at room temperature, the precipitated triethylamine hydrochloride is filtered off and the reaction mixture is worked up as in Example 1. There is obtained 23.5 g (59% of theory) of 1,3-bis-(trichloromethylthio)-hydantoin; m.p. 140°–142° C.

The 3-cyclopropylhydantoin (m.p.: 137°–139° C.) used as starting material was prepared in accordance with A. Mouneyrat (Chem. Ber., 33, 2393, 1900) from cyclopropyl isocyanate and glycocoll.

The compounds in Table 1 below were prepared analogously:

TABLE 1

$$XCCl_2-S-N \quad N-S-CCl_2Y$$

with substituents $R^1$, $R^2$ on the ring.

| Example No. | R¹ | R² | X | Y | m.p. °C. |
|---|---|---|---|---|---|
| 3 | H | H | F | F | 92–94 |
| 4 | H | H | F | Cl | 132–133 |
| 5 | H | —CH₃ | Cl | Cl | 106–108 |
| 6 | H | —CH₃ | F | F | 87–89 |
| 7 | —CH₃ | —CH₃ | Cl | Cl | 114–116 |
| 8 | —CH₃ | —CH₃ | F | F | 88–89 |
| 9 | —CH₃ | —C₂H₅ | Cl | Cl | 110–112 |
| 10 | —CH₃ | —C₂H₅ | Cl | F | 97–98 |
| 11 | —(CH₂)₅— | | Cl | Cl | 148–149 |
| 12 | —(CH₂)₅— | | F | F | 87–88 |

The compounds according to the invention may be converted into the usual formulations, e.g. solutions, emulsions, suspensions, dusts, powders, pastes and granules. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g. chlorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt% of active ingredient.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, pouring, painting or impregnating.

The application rates depend on the effect desired, and range from 0.01 to 3 kg of active ingredient per hectare, or more. Some of the compounds also have a good bactericidal action on bacteria such as *Staphylococcus aureus*. When the active ingredients according to the invention are used to protect materials, fungi such as *Aspergillus niger, Aspergillus flavus, Aspergillus versicolor, Penicillium funiculosum, Chaetomium globosum, Cladosporium herbarum, Pullularia pullulans, Humicola grisea,* and *Sclerophoma pityophila* are combated. When the active ingredients are used to protect materials, e.g., as fungicides for surface coatings and soft PVC, the application rates are from 0.05 to 5% (by weight) of active ingredient, based on the total weight of the paints to be preserved or the PVC to be microbicidally treated. The new active ingredients may also be used as fungicidally effective components of preservatives for protecting wood against wood-discoloring fungi. Application is effected by treating, e.g., impregnating or painting, the wood with these agents.

The agents according to the invention may also be mixed and applied with other active ingredients, e.g., herbicides, insecticides, growth regulators, bactericides, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together.

Examples of fungicides which may be combined with the compounds according to the invention are: dithiocarbamates and their derivatives, e.g. iron (III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene- bis (thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)-disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio(4,5-b)quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorfluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, and 2,6-dimethyl-N-cyclododecylmorpholine and its salts.

In the following experiments demonstrating the fungicidal action of the compounds according to the invention, the following prior art active ingredients were used for comparison purposes:

1,3-bis-(trichloromethylthio)-5-ethyl-5-phenylhydantoin (comparative compound A)

1,3-bis-(trichloromethylthio)-5,5-diphenylhydantoin (comparative compound B).

EXAMPLE 13

*Plasmopara viticola* in grapes

Leaves of potted vines of the Müller-Thurgau variety are sprayed with aqueous dispersions containing (dry basis) 80% (wt%) of the active ingredient and 20% of sodium lignin sulfonate. 0.1, 0.05 and 0.25% (dry basis) spray liquors are used. After the sprayed-on liquor has dried, the leaves are infected with a zoospore suspension of *Plasmopara viticola*. The plants are first placed for 16 hours in a steam-saturated (moist) chamber at 20° C., and then in a greenhouse for 8 days at from 20° to 30° C. To accelerate and intensify the sporangiophore discharge, the plants are then again placed in the moist chamber for 16 hours. The spore sites on the underside of the leaves are then counted; 0 denotes no fungus attack, graduated down to 5, which denotes total attack (control).

| Active ingredient | Leaf attack after spraying with liquor containing active ingredients in amounts of | | |
|---|---|---|---|
| | 0.1% | 0.05% | 0.025% |
| 1 | 0 | 2 | 2 |
| 3 | 0 | 0 | 2 |
| 4 | 0 | 0 | 0 |
| 5 | 0 | 0 | 0 |
| 6 | 0 | 0 | 0 |
| 8 | 0 | 0 | 0 |
| 9 | 0 | 2 | 2 |
| 10 | 0 | 0 | 2 |
| 12 | 0 | 0 | 0 |
| Control (untreated) | 5 | | |

EXAMPLE 14

*Phytophthora infestans* in tomatoes

Leaves of tomatoes of the "Grosse Fleischtomate" variety are sprayed with aqueous dispersions containing (dry basis) 80% (wt%) of active ingredient and 20% of sodium lignin sulfonate. 0.1% (dry basis) spray liquors are used. After the sprayed-on layer has dried, the leaves are infected with a zoospore suspension of *Phytophthora infestans*. The plants are then placed for 5 days in a steam-saturated (moist) chamber kept at 16° C. After this period, the disease has spread on the untreated control plants to such an extent that from 80 to 100% of the leaf surface is covered.

| Active ingredient | Leaf attack after spraying with liquor containing 0.1% of active ingredient |
| --- | --- |
| 1 | 0 |
| 3 | 0 |
| 4 | 0 |
| 5 | 0 |
| 7 | 0 |
| 9 | 0 |
| 12 | 0 |
| A (prior art) | 2 |
| B (prior art) | 2 |
| Control (untreated) | 4 |

0 = no fungus attack, graduated down to 5 = total attack

EXAMPLE 15

*Botrytis cinerea* in pimientos

Pimiento seedlings of the "Neusiedler Ideal Elite" variety with 4 to 5 well developed leaves were sprayed to runoff with 0.1% (wt%) aqueous spray liquors containing (dry basis) 80% of active ingredient and 20% of sodium lignin sulfonate. After the sprayed-on layer had dried, the plants were sprayed with a conidial suspension of the fungus Botrytis cinerea and placed, at 22° to 24° C., in a high-humidity chamber to obtain optimum conditions for fungus growth. After 5 days, the disease had spread on the untreated plants to such an extent that the necroses covered most of the leaf surface.

| Active ingredient | Leaf necroses after spraying with 0.1% liquor |
| --- | --- |
| 5 | 0 |
| 7 | 0 |
| 9 | 2 |
| 10 | 0 |
| A (prior at) | 5 |
| B (prior art) | 5 |
| Control (untreated) | 5 |

0 = no necroses, graduated down to 5 = ⅔ of leaf surface covered with necroses

EXAMPLE 16

*Septoria nodorum* in wheat

Leaves of pot-grown wheat plants of the "Jubilar" variety are sprayed to runoff with aqueous liquors containing 0.2 and 0.1% (wt%) of active ingredient in emulsified form. After the sprayed-on layer has dried, the plants are sprayed with a spore suspension of the fungus *Septoria nodorum* and placed, at 16° to 18° C., in a high-humidity chamber to obtain optimum conditions for fungus growth. After 14 days, the disease has spread on the untreated control plants to such an extent that the leaf blotches cover most of the leaf surface.

| Active ingredient | Leaf attack after spraying with liquor containing active ingredient in amounts of | |
| --- | --- | --- |
| | 0.2% | 0.1% |
| 1 | — | 1 |
| 2 | 3.5 | 3.5 |
| 3 | 2 | 2 |
| 4 | 2 | 2 |
| 5 | 1 | 2 |
| 7 | 1 | 2 |
| 8 | — | 2.5 |
| 9 | 1 | 1 |
| 10 | 2 | 3.5 |
| 11 | 2.5 | 3.5 |
| 12 | — | 2.5 |
| A (prior art) | 5.5 | 5.5 |
| B (prior art) | 4.5 | 4 |
| Control (untreated) | 5.5 | |

0 = no blotches, graduated down to 7 = more than ⅔ of leaf surface covered with blotches

EXAMPLE 17

*Pythium spec.* in pea seedlings

Pea seeds of the "Senator" variety are thoroughly dusted with a disinfectant formulation containing, in triturated form, 40% (wt%) of active ingredient and 60% of talc, in amounts of 0.3 g per 100 g of seed. The seeds treated in this manner are placed, in pots, in soil heavily infected with Pythium. After 21 days, the damage caused by the disease is compared with that on the untreated control plants.

| Active ingredient | Percentages of diseased pea plants (21 days after emergence) |
| --- | --- |
| 1 | 0 |
| 3 | 25 |
| 8 | 0 |
| A (prior art) | 85 |
| B (prior art) | 90 |
| Control (untreated) | 90 |

EXAMPLE 18

*Aspergillus niger*

The active ingredients are added to a nutrient solution ideally suited for promoting the growth of the fungus *Aspergillus niger*, in amounts of 100, 50, 25 and 10 parts by weight per million parts of nutrient solution. 20 ml lots of the nutrient solution treated in this manner are placed in 100 ml glass flasks and inoculated with 0.3 mg of Aspergillus spores. The flasks are incubated at 36° C. for 120 hours, and the extent of fungus spread—predominantly on the surface of the nutrient solutions—is then assessed.

0 = no fungus growth, graduated down to
5 = uncontrolled fungus growth (surface of nutrient solution completely covered by fungus).

| Active ingredient | Amount of active ingredient in nutrient solution in ppm | | | |
| --- | --- | --- | --- | --- |
| | 100 | 50 | 25 | 10 |
| 2 | 0 | 0 | 0 | 0 |
| 4 | 0 | 0 | 2 | 5 |
| 6 | 0 | 0 | 0 | 4 |
| 8 | 0 | 0 | 0 | 4 |
| 10 | 0 | 0 | 0 | 0 |
| 12 | 0 | 0 | 0 | 2 |
| A (prior art) | 5 | 5 | 5 | 5 |
| B (prior art) | 5 | 5 | 5 | 5 |

| | Amount of active ingredient in nutrient solution in ppm | | | |
|---|---|---|---|---|
| Active ingredient | 100 | 50 | 25 | 10 |
| Control (untreated) | 5 | | | |

EXAMPLE 19

90 parts by weight of compound 1 is mixed with 10 parts by weight of N-methyl-α-pyrrolidone. A mixture is obtained which is suitable for application in the form of very fine drops.

EXAMPLE 20

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 21

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isoctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 22

20 parts by weight of compound 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 23

20 parts by weight of compound 5 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 24

3 parts by weight of compound 6 is intimately mixed with 97 parts by weight of particulate kaolin. A dust is obtained containing 3% by weight of the active ingredient.

EXAMPLE 25

30 parts by weight of compound 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 26

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 27

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A 1,3-bis-(trihalomethylsulfenyl)-imidazoline-2,4-dione of the formula

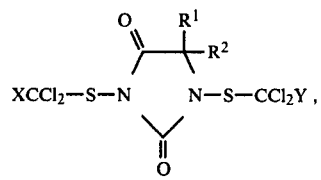

where X and Y are identical or different and each denotes chlorine or fluorine, and $R^1$ and $R^2$ are identical or different and each denotes hydrogen or lower alkyl, or $R^1$ and $R^2$ are directly linked with each other, or together denote the radical $-(CH_2)_n-$, n denoting one of the integers 1, 2, 3, 4, 5 and 6.

2. A 1,3-bis-(trihalomethylsulfenyl)-imidazoline-2,4-dione as claimed in claim 1, where X denotes fluorine, Y denotes fluorine, $R^1$ denotes lower alkyl and $R^2$ denotes hydrogen.

3. A 1,3-bis-(trihalomethylsulfenyl)-imidazoline-2,4-dione selected from the group consisting of 1-dichlorofluoromethylthio-3-trichloromethylthioimidazoline-2,4-dione, 1-trichloromethylthio-3-dichlorofluoromethylthioimidazoline-2,4-dione, and 1,3-bis-(dichlorofluoromethylsulfenyl)-imidazoline-2,4-dione.

4. A process for combating fungi, wherein the objects to be protected against fungus attack are treated with an effective amount of a 1,3-bis-(trihalomethylsulfenyl)-imidazoline-2,4-dione of the formula

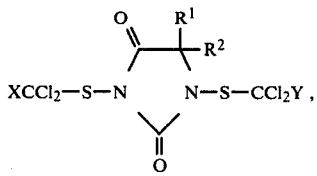

where X and Y are identical or different and each denotes chlorine or fluorine, and $R^1$ and $R^2$ are identical or different and each denotes hydrogen or lower alkyl, or $R^1$ and $R^2$ are directly linked with each other, or together denote the radical $-(CH_2)_n-$, n denoting one of the integers 1, 2, 3, 4, 5 and 6.

* * * * *